United States Patent [19]

Neville Jr. et al.

[11] 4,440,747

[45] Apr. 3, 1984

[54] MONOCLONAL ANTIBODY-RICIN HYBRIDS AS A TREATMENT OF MURINE GRAFT-VERSUS-HOST DISEASE

[75] Inventors: David M. Neville Jr., Bethesda; Richard J. Youle, Kensington, both of Md.

[73] Assignee: The United States of America as represented by the Department of Health and Human Services, Washington, D.C.

[21] Appl. No.: 350,223

[22] Filed: Feb. 19, 1982

Related U.S. Application Data

[63] Continuation-in-part of Ser. No. 186,735, Sep. 30, 1980, Pat. No. 4,359,457.

[51] Int. Cl.$^3$ ............................................. A61K 39/00
[52] U.S. Cl. ..................................... 424/85; 424/101; 604/28
[58] Field of Search ............................. 424/8, 12, 85; 260/112 R, 112 B; 604/28

[56] References Cited

U.S. PATENT DOCUMENTS 4,340,535 7/1982 Voisin et al. .......................... 424/85
4,359,457 11/1982 Neville ............................ 424/177 X

FOREIGN PATENT DOCUMENTS 44167 1/1982 European Pat. Off. .

OTHER PUBLICATIONS

Letarte, Chem. Abs., vol. 93, 1980, Ab. No. 93:202498z.
Oeltmann Chem. Abs., vol. 95, 1981, Ab. No. 95:78306k.
Thorpe, Chem. Abs., vol. 95, 1981, Ab. No. 95:22810c.
Pau, Chem. Abs., vol. 94, 1981, Ab. No. 94:132084j.
Cotmore, Eur. J. Immunol., vol. 11, 1981, pp. 597–603.
Youle, PNAS, vol. 77, No. 9, Sep. 1980, pp. 5483–5486.
Neville, Biochem. Soc. London Trans., vol. 8, No. 6, 1980, pp. 692–693.
Moulten, Proc. Amer. Asso. Cancer Res., Abs., vol. 15, 1974, p. 24, Ab. No. 94.
Jansen Immunobiol., vol. 157, No. 3, 1980, pp. 229–230.
Saxena, Immunol. Communications, vol. 9, No. 4, 1980, pp. 371–378.

Primary Examiner—Sam Rosen
Attorney, Agent, or Firm—John S. Roberts, Jr.

[57] ABSTRACT

The receptor specificity of toxins can be altered by coupling the intact toxin to monoclonal antibodies directed to the cell surface antigen Thy 1.2. Monoclonal antibody Thy 1.2-ricin (or ricin A chain) is a pretreatment reagent used to eliminate graft-versus-host disease (GVHD) in bone marrow transplants.

2 Claims, 3 Drawing Figures

MONOCLONAL ANTIBODY-RICIN HYBRIDS AS A TREATMENT OF MURINE GRAFT-VERSUS-HOST DISEASE

This application is a continuation-in-part application of Ser. No. 186, 735 filed Sept. 30, 1980 and now U.S. Pat. No. 4,359,457, Anti-thy 1.2 Monoclonal Antibody-Ricin Hybrid Utilized as a Tumor Suppressant.

PRIOR ART

Neville, D. M., and R. Youle, Monoclonal Antibody-Ricin or Antibody-Ricin A Chain Hybrids: Kinetic Analysis of Cell Killing for Tumor Therapy, *Immunology Reviews*, Vol. 62, p 135, (1981).

Roitt, Ivan, *Essential Immunology*, 4th Edition, Boston, Mass.: Blackwell Scientific Publications, 1980.

Youle, R. J., and D. M. Neville, Jr., Anti-Thy-1.2 Monoclonal Antibody Linked to Ricin is a Potent Cell Type Specific Toxin, *Proc. National Academy of Science*, USA, Vol. 77, p 5483 (1980).

Youle, R. J., G. T. Murray, and D. M. Neville, Jr., Studies on the Galactose Binding Site of Ricin and the Hybrid Toxin Man-6P-Ricin, Cell, Vol. 23, p. 551 (1981).

Vallera, Daniel A., Richard J. Youle, David M. Neville, Jr., John H. Kersey, Bone Marrow Transplantation Across Major Histocompatibility Barriers, (in press).

U.S. Ser. No. 186,735 filed Sept. 12, 1980, now U.S. Pat. No. 4,359,457, Anti-Thy 1.2 Monoclonal Antibody-Ricin Hybrid Utilized as a Tumor Suppressant.

U.S. Ser. No. 199,781 filed Oct. 23, 1980, now U.S. Pat. No. 4,356,117, Chemical Modifications of Proteins Which Induce New Receptor Specificities and Therefore Elicit New Effects in Cells.

U.S. Ser. No. 341,572 filed Jan. 21, 1982, Ricin and Modeccin Reagents Effective as Tumor Suppressive Cytotoxic Reagents (cip of Ser. No. 199,781 filed Oct. 23, 1980).

The ability to change the specificity of toxin is known. However, the mechanism pathway used to enter eucharyotic ribosomes was not understood. Recent developments have shown that antibody conjugates to either the intact ricin (both A and B chain) or the A chain subunit of ricin carry the antibody into the ribosome. This knowledge led to advances in the state of the art as reflected in this application.

The advances shown in previous applications led to the discoveries herein reported. Ser. No. 199,781 (filed Oct. 23, 1980) and the continuation-in-part application to that application, Ser. No. 341,572 (filed Jan. 21, 1981), teach a tumor suppressant active against leukemia, a cytotoxic reagent consisting of mannose-6-phosphate-modeccin, and a reagent which inhibits cholesterol synthesis. These discoveries were instrumental in showing the role of the B chain subunit of ricin and the necessity of adding excess lactose to bind some of the ricin receptors.

Ser. No. 186,735 (filed Sept. 12, 1980) is the second in a series of three which provide greater understanding to altering toxin specificities. Ser. No. 186,735 teaches the use of monoclonal antibody Thy 1.2-ricin as a murine lymphoma cancer suppressant. Again, the invention dealt with the intact ricin and was shown specific for lymphoma cancer.

The present invention, the third in the series, teaches the use of ricin in combination with Thy 1.2 as a pretreatment regimen to protect mice from lethal graft-versus-host-disease during bone marrow transplant operations. This is most crucial in the treatment of diseases such as leukemia which, up until now, have shown limited success with the bone marrow transplant method.

This invention also teaches the importance of ricin A chain subunit both in the treatment of GVHD and in tumor suppressant reagents. Thy 1.1 linked to ricin A chain subunit is useful for tumor suppression for cells with a Thy 1.1 receptor. This mechanism pathway is detailed below.

BACKGROUND

The earliest hybrid toxins (constructed with peptide hormones) were unable to demonstrate toxicity. Later hybrids demonstrated specific cytotoxicity, but performed badly; i.e., the hybrid toxicity was less effective than the parent toxin. More recently, however, several hybrids have shown both a high degree of selectivity and potency against tumor cells. A variety of tests indicated that entry of "A" chain subunits of ricin into the cytosol compartment was facilitated by either certain classes of receptors or by certain toxin binding chains. Later tests showed that receptors which were used to internalize lysosomal hydrolyses (hydrolysis catalyst found in lysosomes) into the lysosomal compartment, mannose-6-phosphate receptors, could also efficiently internalize the hybrid mannose-6-phosphate-ricin into the cytosol compartment and inactivate protein synthesis. Excess lactose in the medium was used to block the usual ricin entry route via its receptor. Experiments then showed that a binding site on the ricin B chain was necessary for the efficient entry of mannose-6-phosphate ricin into the cytosol compartment. This invention teaches new ricin hybrids with a binding chain consisting of a monoclonal antibody with an affinity for the murine thymic adult differentiation antigen, Thy 1.1 or Thy 1.2. The monoclonal antibody is thioether linked to an intact ricin.

UTILITY STATEMENT

This invention is useful in two major areas of mammalian immunological systems. Monoclonal antibody Thy 1.1-ricin is effective as a tumor killing agent, sustaining more rapid killing and a lower fraction of survivors. Monoclonal antibody Thy 1.2-ricin is a unique and powerful pretreatment reagent to control graft versus host disease in bone marrow transplantation. In either case the treatment protocols are simple, the risk of toxic effects against host tissue is minimized, and treatment of donor bone marrow in vitro is facilitated prior to transplantation across major histocompatibility barriers. The use of these monoclonal antibodies are a major advance because the reagent is uniquely defined, can be reproduced at will, and does not require adsoption protocols which are difficult to standardize.

BRIEF SUMMARY OF THE PROCESS

Killing cells involves three sequential steps: (1) binding the toxin to the cell surface; (2) transporting the toxin to the cytosol compartment; and (3) catalytic inactivation of an essential component of protein synthesis. The binding sequence involves ricin toxin, composed of two separable components which have distinct roles in cell-killing: the A chain subunit and the B chain subunit. The A chain, containing sites for binding with the monoclonal antibody, Thy 1.1 and Thy 1.2, enzymatically inactivates eukaryotic ribosomes inhibiting protein synthesis; the B chain binds the protein to galactose-containing cell surface receptors common to all mammalian cells. The native binding specificity of ricin can be modified to that dictated by covalently bound monoclonal anti-Thy 1.1 (or anti-Thy 1.2) following competitive blocking (using excess lactose) of the galatose-binding site on the B chain. The resulting protein hybrid is selectively toxic in vitro for Thy-bearing cells. By flooding the medium with lactose (which binds to the B chain subunit) the ricin hybrid becomes specific for the tumor cells.

Once the hybrid binds with the cell, the second step begins as the hybrid is encapsulized in an interior compartment of the cell. This is an endocytotic vesicle called the cytosol, and this sequence is termed internalization. Once internalization is complete, the third step begins: the A and B chains cross the cytosol wall and attach to the ribosomes, protein synthesizing machinery. The A chain subunit destroys ribosomes by substituting part of its ingredients for part of the protein. This substitution destroys the cell.

This proces may occur using the A chain alone (linked with monoclonal antibody). However, the B chain facilitates crossing the cytosol barrier into the proteins, thus increasing the efficiency and rate of destroying the tumor cells beyond the capability of the A chain subunit by itself.

SPECIFIC EMBODIMENTS

Monoclonal antibody Thy 1.1 or Thy 1.2 are not ordinarily toxic; in order to make them toxic, however, toxin ricin is covalently linked with the antibody. Ricin ordinarily binds, enters, and kills cells through receptors containing galactose. The hybrid protein, anti-Thy 1.1-ricin or anti-Thy 1.2-ricin, can enter and kill cells via the Thy 1.1 or Thy 1.2 receptor.

An intact ricin, composed of two subunits, an A chain and a B chain, contains certain types of binding sites. The A chain subunit of ricin, linked with the monoclonal antibody Thy 1.1 or Thy 1.2, is an enzyme which inactivates the eukaryotic ribosome, thus halting protein production. However, the binding of the toxin to the cell occurs only via the B subunit. The ricin B chain increases the entry rate of the antibody directed A chain into the cytosol compartment. The efficiency of the entry process is increased independent of the amount of hybrid bound to surface receptors. When cells are exposed to ricin toxin, the rate of protein synthesis decreases exponentially with time.

FIG. 1 shows the effect on cells for ricin at two different concentrations. Hybrids of ricin can be constructed by adding a new receptor binding moiety. This hybrid has two binding sites—one specific for the target cell and one for all cell types via the ricin receptor. The latter binding site can be partially blocked by the addition of exogenous lactose which binds to the ricin B chain, thereby inhibiting this entry route and forcing binding at the Thy 1.1 or Thy 1.2 site. The advantage of constructing these hybrids with intact ricin (as opposed to A chain or B chain alone) is that these hybrids not only show protein inactivation rates similar to ricin, they also are specific for certain cells. In addition, Thy 1.1 and Thy 1.2 are low affinity antibodies; they require the ricin B chain to achieve the necessary entry rate and low fraction of cell survivors. These hybrids, then, effectively kill target cells without destroying nearby non-target cells.

EXAMPLES

Tests were run according to the specifications herein detailed.

EXAMPLE 1

C57BL/6 mice were immunosuppressed by total body X-irradiation with 900 rads. Bone marrow cells ($2.5 \times 10^7$) were mixed with an equal number of spleenocytes from Balb/c mice and injected i.v. into the H-2 incompatible, irradiated C57BL/6 mice. The C57BL/6 mice died from graft versus host disease (GVHD) as shown (Allo BMS). When the donor cells were first treated with anti-Thy 1.2 antibody then injected into C57BL/6 mice, a small but significant delay in mortality was found (Allo BMS and Thy 1.2). When donor cells were treated with 0.5 ug/ml anti-Thy 1.2-ricin plus 200 mM lactose, 91% of the mice survived to 70 days (Allo BMS+Thy 1.2-ricin). Thus, the hybrid protected the mice from lethal GVHD while the antibody alone did not. Also, when donor cells were treaed with anti-Thy 1.2 plus complement, all of the mice lived to 70 days with no sign of GVHD (Allo BMS+Thy 1.2+C). When donor cells were treated with complement alone, all mice died from GVHD by 35 days (Allo BMS+C). When mice were treated with syngeneic donor cells obtained from C57BL/6 mice, all mice survived (Syn BMS).

Figure 3:
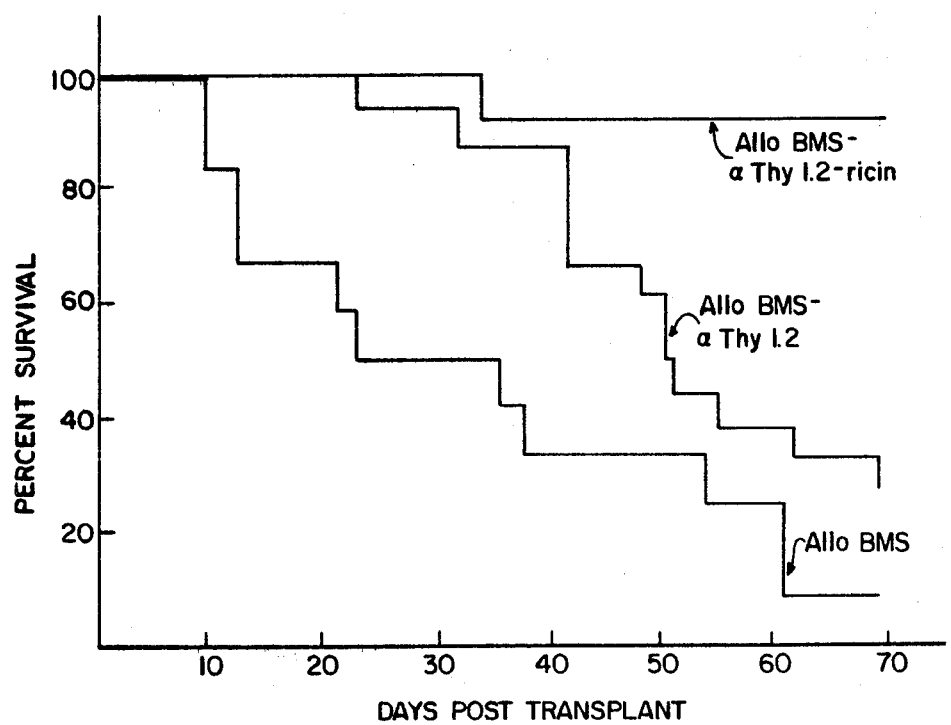
FIG. 3 reflects the percent survival rate of mice for three different reagents when used in the pretreatment regimen of a bone marrow transplant.

The results of this experiment are tabulated in FIG. 3.

EXAMPLE 2

Figure 1:
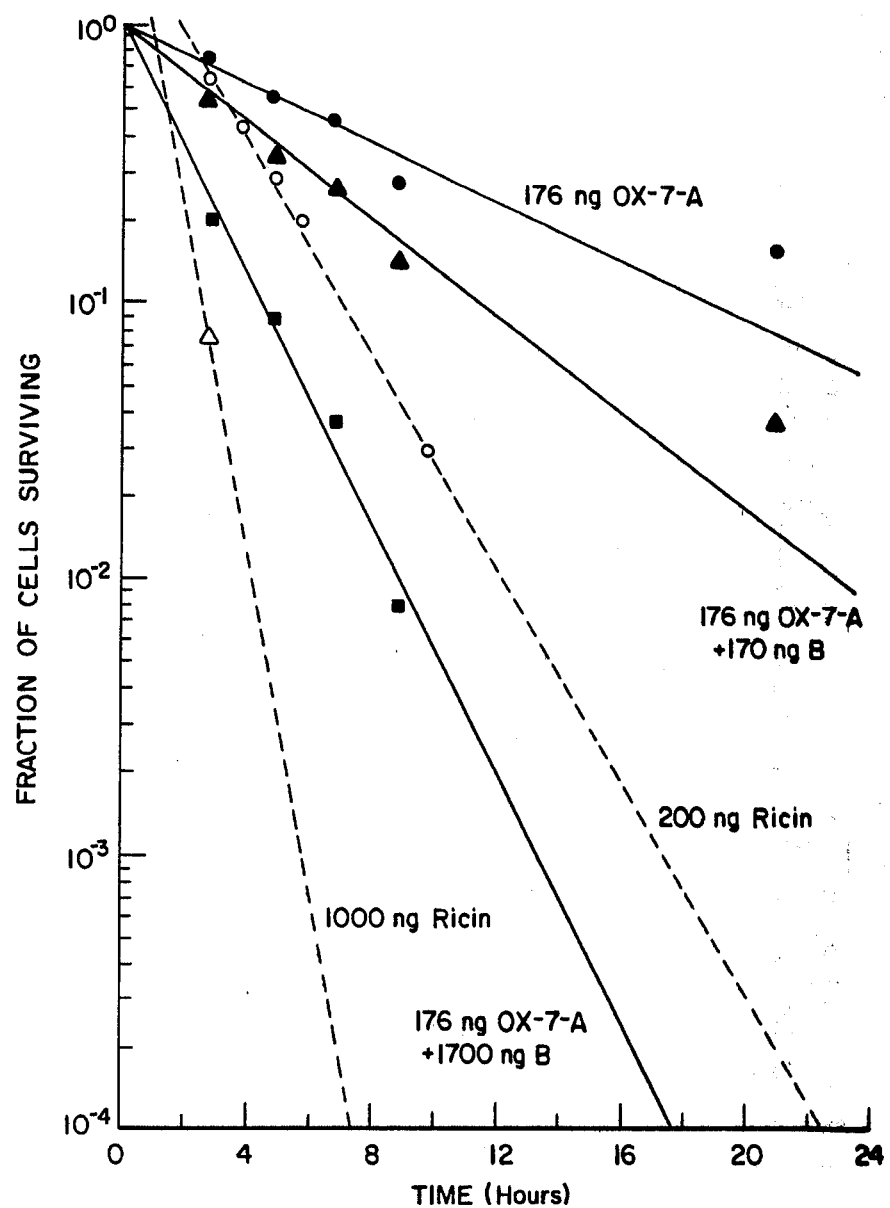
FIG. 1 compares OX-7-A (monoclonal antibody Thy 1.1), Thy 1.1 plus ricin, and ricin alone.

Anti-Thy 1.1 monoclonal antibody, OX-7, was purchased on the market. A comparison effectiveness of target cell-killing was conducted using the antiody linked to ricin A chain (OX-7-A), OX-7-A plus ricin B chain, and ricin alone. FIG. 1 shown the results of these comparisons using different concentrations.

EXAMPLE 3

Figure 2:
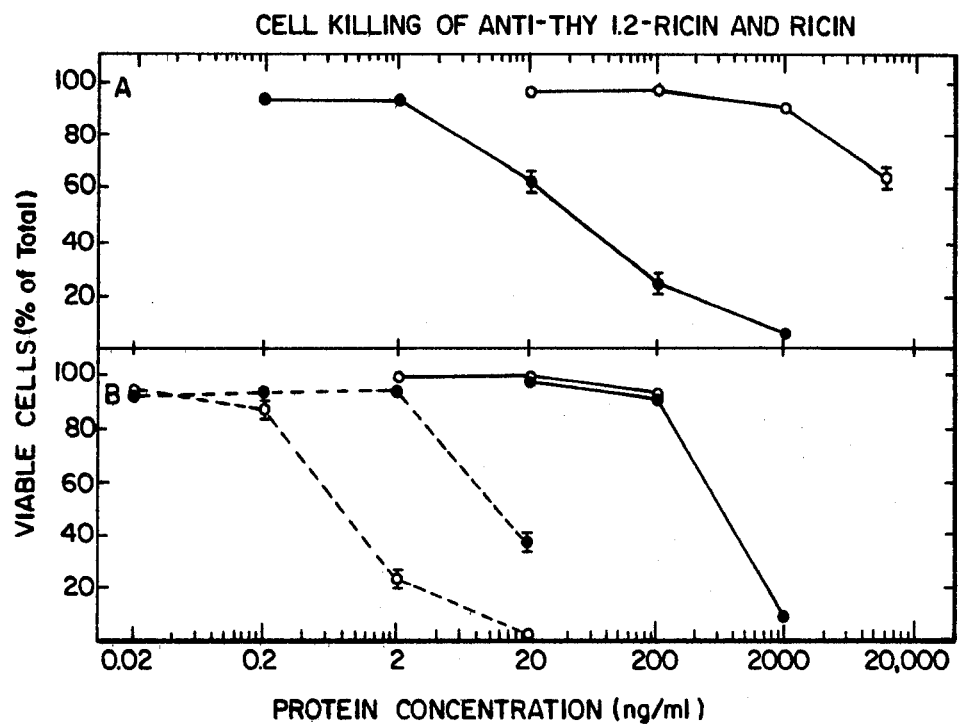
FIG. 2 shows the effect of concentration of toxin or hybrid.

The effect of dose-response of anti-Thy 1.2-ricin (upper, A) and ricin (lower, B) on EL-4 and AKR cell viability was tested. In spite of the selectiity between target and non-target cells, the killing curves were shallow for the hybrid. Cell viability was assayed by trypan blue exclusion after a 3-day exposure to the toxins. FIG. 2 shows the results. (A) Anti-Thy 1.2-ricin plus 50 mM lactose: ●———●, on EL-4 cells; ○———○, on AKR-K36 cells. (B) Ricin plus 50 mM lactose: ●———●, on EL-4 cells; ○———○, on AKR-K36 cells. Ricin alone: ●-----●, on EL-4 cells; ○-----○, on AKR-K36 cells.

We claim:

1. A process for the treatment of graft versus host disease comprising
   removing bone marrow cells from a murine donor;
   in vitro treating the donor cells with anti-thy 1.2-ricin in the presence of excess lactose; and
   injecting the treated cells into a murine recipient.

2. A process using monoclonal antibody anti-thy 1.2-ricin for the pretreatment of murine graft versus host disease comprising
  removing bone marrow cells from mice exhibiting graft versus host disease;
  combining in vitro said bone marrow cells with monoclonal antibody anti-thy 1.2-ricin in the presence of excess lactose;
  injecting said treated bone marrow cells into a murine recipient.

* *